(12) United States Patent
Zhou et al.

(10) Patent No.: US 7,391,520 B2
(45) Date of Patent: Jun. 24, 2008

(54) FOURIER DOMAIN OPTICAL COHERENCE TOMOGRAPHY EMPLOYING A SWEPT MULTI-WAVELENGTH LASER AND A MULTI-CHANNEL RECEIVER

(75) Inventors: Yan Zhou, Pleasanton, CA (US); Matthew J. Everett, Livermore, CA (US)

(73) Assignee: Carl Zeiss Meditec, Inc., Dublin, CA (US)

( * ) Notice: Subject to any disclaimer, the term of this patent is extended or adjusted under 35 U.S.C. 154(b) by 215 days.

(21) Appl. No.: 11/174,158

(22) Filed: Jul. 1, 2005

(65) Prior Publication Data

US 2007/0002327 A1    Jan. 4, 2007

(51) Int. Cl.
*G01B 9/02* (2006.01)

(52) U.S. Cl. ........................... 356/479; 356/497
(58) Field of Classification Search .......... 356/479, 356/497
See application file for complete search history.

(56) References Cited

U.S. PATENT DOCUMENTS

| | | | |
|---|---|---|---|
| 4,896,325 A | 1/1990 | Coldren | 372/20 |
| 5,202,745 A | 4/1993 | Sorin et al. | 356/73.1 |
| 5,325,392 A | 6/1994 | Tohmori et al. | 372/96 |
| 5,459,570 A | 10/1995 | Swanson et al. | 356/345 |
| 5,956,355 A | 9/1999 | Swanson et al. | 372/20 |
| 6,160,826 A | 12/2000 | Swanson et al. | 372/20 |
| 6,432,736 B1 | 8/2002 | Lee et al. | 438/34 |
| 6,617,188 B2 | 9/2003 | Ooi et al. | 438/36 |
| 6,657,727 B1 | 12/2003 | Izatt et al. | 356/450 |
| 6,847,661 B2 | 1/2005 | Jerman et al. | 372/20 |
| 6,878,562 B2 | 4/2005 | Ooi et al. | 438/22 |
| 6,970,654 B1 * | 11/2005 | Paglione et al. | 398/182 |

2003/0128724 A1    7/2003    Morthier .................... 372/20

(Continued)

FOREIGN PATENT DOCUMENTS

JP    2000-046729    2/2000

(Continued)

OTHER PUBLICATIONS

T. Amano et al., "Optical Frequency-domain reflectometry with a rapid wavelength-scanning superstructure-grating distributed Bragg reflector laser," *Applied Optics*, vol. 44, No. 5, Feb. 10, 2005, pp. 808-816.

(Continued)

*Primary Examiner*—Tarifur R Chowdhury
*Assistant Examiner*—Jonathan M Hansen
(74) *Attorney, Agent, or Firm*—Stallman & Pollock LLP

(57) ABSTRACT

The present invention is an alternative Fourier domain optical coherence system (FD-OCT) and its associated method. The system comprises a swept multi-wavelength laser, an optical interferometer and a multi-channel receiver. By employing a multi-wavelength laser, the sweeping range for each lasing wavelength is substantially reduced as compared to a pure swept single wavelength laser that needs to cover the same overall spectral range. The overall spectral interferogram is divided over the individual channels of the multi-channel receiver and can be re-constructed through processing of the data from each channel detector. In addition to a substantial increase in the speed of each axial scan, the cost of invented FD-OCT system can also be substantially less than that of a pure swept source OCT or a pure spectral domain OCT system.

32 Claims, 10 Drawing Sheets

U.S. PATENT DOCUMENTS

| | | | |
|---|---|---|---|
| 2003/0193974 A1* | 10/2003 | Frankel et al. | 372/20 |
| 2004/0228384 A1 | 11/2004 | Oh et al. | 372/96 |
| 2004/0239938 A1 | 12/2004 | Izatt | 356/450 |
| 2005/0018201 A1* | 1/2005 | de Boer et al. | 356/479 |
| 2005/0035295 A1 | 2/2005 | Bouma et al. | 250/341.1 |
| 2006/0244973 A1* | 11/2006 | Yun et al. | 356/511 |

FOREIGN PATENT DOCUMENTS

| | | |
|---|---|---|
| JP | 2001-174404 | 6/2001 |
| WO | WO 03/062802 A2 | 7/2003 |
| WO | WO 03/073041 A1 | 9/2003 |
| WO | WO 2004/043245 A1 | 5/2004 |
| WO | WO 2005/022709 A1 | 3/2005 |
| WO | WO 2005/047813 A1 | 5/2005 |
| WO | WO 2006/039091 A2 | 4/2006 |

OTHER PUBLICATIONS

P. Andretzky et al., "Optical Coherence Tomography by 'Spectral Radar': Improvement of Signal-to-Noise Ratio," *SPIE*, vol. 3915 (2000), pp. 55-59.

A. Behfar et al., "Etching Advances," *SPI;s oemagazine*, Feb. 2005, 3 pages in length.

B. Cense et al., "Ultrahigh-resolution high-speed retinal imaging using spectral-domain optical coherence tomography," *Optics Express*, vol. 12, No. 11, May 31, 2004, pp. 2435-2447.

S.R. Chinn et al., "Optical coherence tomography using a frequency-tunable optical source," *Optics Letters*, vol. 22, No. 5, Mar. 1, 1997, pp. 340-342.

M.A. Choma et al., "Sensitivity advantage of swept source for Fourier domain optical coherence tomography," *Optics Express*, vol. 11, No. 18, Sep. 8, 2003, pp. 2183-2189.

J.F. de Boer et al., "Improved signal-to-noise ratio in spectral-domain compared with time-domain optical coherence tomography," *Optics Letters*, vol. 28, No. 21, Nov. 1, 2003, pp. 2067-2069.

X. Fang et al., "A Subnanosecond Polarization-Independent Tunable Filter/Wavelength Router Using a Sagnac Interferometer," *IEEE Photonics Technology Letters*, vol. 9, No. 11, Nov. 1997, pp. 1490-1492.

C.M. Greiner et al., "Wavelength division multiplexing based on apodized planar holographic Bragg reflectors," *Applied Optics*, vol. 43, No. 23, Aug. 10, 2004, pp. 4575-4583.

T. Haber et al., "Tunable Erbium-Doped Fiber Ring Laser Precisely Locked to the 50-GHz ITU Frequency Grid," *IEEE Photonics Technology Letters*, vol. 12, No. 11, Nov. 2000, pp. 1456-1458.

G. Häusler et al., "'Coherence Radar' and 'Spectral Radar'—New Tools for Dermatological Diagnosis," *Journal of Biomedical Optics*, vol. 3. No. 1, Jan. 1998, pp. 21-31.

D. Hölscher et al., "Chirp Optical Coherence Tomography with High Resolution and Artifact Reduction Using Tunable Near-Infrared Laser," *SPIE*, vol. 3251 (1998), pp. 68-75.

R. Huber et al., "Amplified, frequency swept lasers for frequency domain reflectometry and OCT imaging: design and scaling principles," *Optics Express*, vol. 13, No. 9, May 2, 2005, pp. 3513-3528.

M. Ibsen et al., "Sinc-Sampled Fiber Bragg Gratings for Identical Multiple Wavelength Operation," *IEEE Photonics Technology Letters*, vol. 10, No. 6, Jun. 1998, pp. 842-844.

S. Janz et al., "Planar Waveguide Echelle Gratings in Silica-On-Silicon," *IEEE Photonics Technology Letters*, vol. 16, No. 2, Feb. 2004, pp. 503-505.

V. Jayaraman et al., "Theory, Design, and Performance of Extended Tuning Range Semiconductor Lasers with Sampled Gratings," *IEEE Journal of Quantum Electronics*, vol. 29, No. 6, Jun. 1993, pp. 1824-1834.

R. Leitgeb et al., "Performance of fourier domain vs. time domain optical coherence tomography," *Optics Express*, vol. 11, No. 8, Apr. 21, 2003, pp. 889-894.

Z. Ma et al., "High-speed spectral domain optical coherence tomography for imaging of biological tissues," *Proceedings of SPIE (Optics in Health Care and Biomedical Optics: Diagnostics and Treatment II)*, vol. 5630 (2005) pp. 286-294.

T. Mitsui, "Dynamic Range of Optical Reflectometry with Spectral Interferometry," *Jpn. J. Appl. Phys.*, vol. 38, Part 1, No. 10, Oct. 1999, pp. 6133-6137.

N. Nassif et al., "In vivo human retinal imaging by ultrahigh-speed spectral domain optical coherence tomography," *Optics Letters*, vol. 29, No. 5, Mar. 1, 2004, pp. 480-482.

M. Nikoufard et al., "An 8×25 GHz polarization-independent integrated multi-wavelength receiver," *Integrated Photonics Research Topical Meeting, Proc. IPR 2004*, Jun. 30 through Jul. 4, 2004, San Francisco USA 2004, ITHB2, 3 pages in length.

W.Y. Oh et al., "Wide Tuning Range Wavelength-Swept Laser With Two Semiconductor Optical Amplifiers," *IEEE Photonics Technology Letters*, vol. 17, No. 3, Mar. 2005, pp. 678-680.

V.I. Tolstikhin et al., "44-channel optical power monitor based on an echelle grating demultiplexer and a waveguide photodetector array monolithically integrated on an InP substrate," *Optical Fiber Communications Conference, Atlanta, Postdeadline Paper* (2003), PD37, 3 pages in length.

V. Vilokkinen et al., "Reliability analysis of AlGaInAs lasers in 1.3 µm," *Electronics Letters*, vol. 40, No. 23, Nov. 11, 2004, pp. 1489-1490.

M. Wojtkowski et al., "Real-time in vivo imaging by high-speed spectral optical coherence tomography," *Optics Letters*, vol. 28, No. 19, Oct. 1, 2003, pp. 1745-1747.

M. Wojtkowski et al., "Ultrahigh-resolution, high-speed, Fourier domain optical coherence tomography and methods for dispersion compensation," *Optics Express*, vol. 12, No. 11, May 31, 2004, pp. 2404-2422.

J. Yao et al., "Multiwavelength Erbium-Doped Fiber Ring Laser Incorporating an SOA-Based Phase Modulator," *IEEE Photonics Technology Letters*, vol. 17, No. 4, Apr. 2005, pp. 756-758.

S.H. Yun et al., "High-speed optical frequency-domain imaging," *Optics Express*, vol. 11, No. 22, Nov. 3, 2003, pp. 2953-2963.

S.H. Yun et al., "High-speed spectral-domain optical coherence tomography at 1.3 µm wavelength," *Optics Express*, vol. 11, No. 26, Dec. 29, 2003, pp. 3598-3604.

S.H. Yun et al., "Extended-Cavity Semiconductor Wavelength-Swept Laser for Biomedical Imaging," *IEEE Photonics Technology Letters*, vol. 16, No. 1, Jan. 2004, pp. 293-295.

S.H. Yun et al., "Removing a depth-degeneracy in optical frequency domain imaging with frequency shifting," *Optics Express*, vol. 12, No. 20, Oct. 4, 2004, pp. 4822-4828.

J. Zhang et al., "Removal of a mirror image and enhancement of the signal-to-noise ratio in Fourier-domain optical coherence tomography using an electro-optic phase modulator," *Optics Letters*, vol. 30, No. 2, Jan. 15, 2005, pp. 147-149.

A.V. Zvyagin, "Fourier-domain optical coherence tomography: optimization of signal-to-noise ratio in full space," *Optics Communications*, vol. 242 (2004) pp. 97-108.

Brochure, Laser & ASE Systems, "Rapid Scan Tunable Lasers," *Thorlab Inc. Product Catalog*, vol. 17 (2005),1 page in length.

In re U.S. Appl. No. 60/629,429, filed Nov. 19, 2004, by Yan Zhou et al., entitled "High efficiency balanced detection interferometer design employing a 3×3 coupler and a circulator in a looped sample path," 41 pages in length.

S.H. Yun et al., "Pulsed-source and swept-source spectral-domain optical coherence tomography with reduced motion artifacts," *Optics Express*, vol. 12, No. 23, Nov. 15, 2004, pp. 5614-5624.

S.H. Yun et al., "High-speed wavelength-swept semiconductor laser with a polygon-scanner-based wavelength filter," *Optic Letters*, vol. 28, No. 20, Oct. 15, 2003, pp. 1981-1983.

* cited by examiner

FOURIER DOMAIN OPTICAL COHERENCE TOMOGRAPHY EMPLOYING A SWEPT MULTI-WAVELENGTH LASER AND A MULTI-CHANNEL RECEIVER

BACKGROUND OF THE INVENTION

1. Field of the Invention

The invention relates generally to optical coherence tomography (OCT) and in particular to Fourier domain optical coherence tomography.

2. Description of Related Art

Optical Coherence Tomography (OCT) is a technology for performing high-resolution cross sectional imaging that can provide images of tissue structure on the micron scale in situ and in real time. In recent years, it has been demonstrated that Fourier domain OCT (FD-OCT), which so far employs either a wavelength swept source and a single detector or a broadband source and an array spectrometer, has significant advantages in both speed and signal-to-noise ratio as compared to time domain OCT (TD-OCT). In TD-OCT, the optical path length between the sample and reference arms needs to be mechanically scanned. For example, patent application WO03062802 (EP1470410, CA2474331, US20050018201) is a hybrid time and spectral domain OCT system in which a broadband source is combined with sub-depth range mechanical optical path length scanning and parallel detection of a set of optical spectral bands. This design can increase the signal-to-noise ratio and at the same time reduce the mechanical scanning range. But mechanical scanning is still required and the A-scan speed is thus limited.

In both swept source OCT (SS-OCT) and spectrometer-based spectral domain OCT (SD-OCT), the optical path length difference between the sample and reference arm is not mechanically scanned, instead, a full axial scan (also called A-scan) is obtained in parallel for all points along the sample axial line within a short time determined by the wavelength sweep rate of the swept source (in SS-OCT) or the line scan rate of the line scan camera (in SD-OCT). As a result, the speed for each axial scan can be substantially increased as compared to the mechanical scanning speed of TD-OCT and this is especially beneficial for real-time imaging of movable biological samples such as the human eye. In addition, SD-OCT and SS-OCT can provide substantially greater signal-to-noise ratio relative to TD-OCT, as explained by Mitsui and others ("Dynamic Range of Optical Reflectometry with Spectral Interferometry." *Japanese Journal of Applied Physics* 38(10): 6133-6137). There are a number of patents as well as articles that either disclosed the basic concept of or discussed the advantages of Fourier domain OCT using either a swept single wavelength source combined with a single photodetector or a broadband source combined with an array spectrometer. Several of these articles and patents are listed separately under the REFERENCES section. These and other articles and patents cited are all incorporated herein as references of this invention.

However, these prior arts are based on purely employing either a swept single wavelength source combined with a single photodetector (thereafter called pure swept-source OCT or pure SS-OCT) or a broadband source combined with an array spectrometer, comprising an optical spectral dispersing element and an array of photodetectors (thereafter called pure spectral-domain OCT or pure SD-OCT). A pure SS-OCT or a pure SD-OCT system each has its advantages and disadvantages in terms of cost, speed, size, stability and other factors as will be elaborated shortly. Based on the advantages of FD-OCT and most importantly, the cost of currently available optical components, we describe an alternative FD-OCT system that not only retains the advantageous features of a pure SS-OCT and a pure SD-OCT, but also saves the cost of the overall system and increases the speed.

In order to fully appreciate the novel features of the present invention, let us first take a brief look at a pure SS-OCT system and a pure SD-OCT system. FIG. 1 shows the basic configuration of a pure SS-OCT system. Light from a tunable single wavelength laser 102 is split through a beam splitter or fiber coupler 104 into a reference arm 106 and a sample arm 108 of an interferometer and the interference signal is detected with a single high-speed photodetector 110. By sweeping the wavelength of the monochromatic source 102, the spectral interferogram of the OCT interferometer is recorded sequentially. The axial reflectance distribution of the sample is obtained by a Fourier transform of the sequentially acquired detector signal. The most advantageous feature of a pure SS-OCT system, compared to other FD-OCT systems, is its compactness and simplicity. For example, patent application US20050035295 and the article by Oh, W. Y. et al. ("Wide tuning range wavelength-swept laser with two semiconductor optical amplifiers." *Photonics Technology Letters, IEEE* 17(3): 678-680) disclosed a wavelength tuning source for SS-OCT that employs a continuously rotating optical arrangement for lasing wavelength selection. In this prior art, a single rotating polygon can be combined with two (or more) gratings and two (or more) optical amplifiers of different optical gain bandwidth to generate a combined wide band wavelength scanning light. The combined output can be synchronized because of the use of a single rotating polygon to provide a continuous linear wavelength tuning over a wide spectral range. However, the current price of a swept source that meets the specification requirement of a practical pure SS-OCT system is very high (see for example, Thorlab Inc. *Product Catalog*, Vol. 17, (2005) page 469) and in addition, the demonstrated wavelength sweep rate is limited to about 20 kHz (Oh, W. Y. et al. (2005). "Wide tuning range wavelength-swept laser with two semiconductor optical amplifiers." *Photonics Technology Letters, IEEE* 17(3): 678-680). Furthermore, commercial products currently having a high price tag are still in the stage of further development, whereas tunable semiconductor lasers developed for optical fiber communications either are step-tuned to fit the ITU grid (see for example, Amano, T. et al. (2005). "Optical frequency-domain reflectometry with a rapid wavelength-scanning superstructure-grating distributed Bragg reflector laser." *Applied Optics* 44(5): 808-816) or, if continuously tunable, are very slow (see for example, U.S. Pat. No. 6,847,661) and they do not meet the requirement for a pure SS-OCT system, such as the high wavelength sweeping rate (more than 20 kHz) and the broad spectral range to be covered (e.g. 25 to 200 nm).

FIG. 2 shows the basic configuration of a pure SD-OCT system. Its difference from a pure SS-OCT system is that instead of a wavelength swept laser and a single detector, a broadband source 202 is used and a grating 212 disperses the interfered optical wave to a photodetector array 214. The main disadvantage of a pure SD-OCT system is the bulky size of the spectrometer 216 and the output sensitivity of the spectrometer 216 to mechanical vibration and temperature change. One advantage is the relatively lower cost of the superluminescent diode (~$1 k) that can be used as the source 202 and a Si (silicon) based line scan camera ($2 k~$4 k) that can be used as the detector array 214. However, a Si based line scan camera has a limited wavelength response range from 0.25 to 1.1 µm. While this wavelength range is appropriate for some biological imaging applications, longer wavelengths are advantageous in many other applications. For example, melanin pigment and hemoglobin are less absorptive for wavelengths between 1 and 2 μm than for visible light. For OCT in the front portions of the human eye, wavelengths longer than 1 μm offer the advantage of higher illumination power without exceeding eye-safety limits, because water in the eye largely absorbs light of these wavelengths before it reaches the sensitive human retina. As Si cannot cover this wavelength range, InP or InGaAs based detector array appears to be the only practical alternative. Unfortunately, the current price of InP or InGaAs based photodetector array is very high and the line scan rate of these detector arrays is limited to 10 kHz range.

A need therefore exists for an alternative FD-OCT design that can take the speed advantage of FD-OCT without requiring a high-speed array detector, or a high-speed wide-range swept laser source.

The sweep range and sweep speed of a continuously tunable laser are generally limited by the swept filter acting as a tuning element. In addition, laser dynamics limits the sweep speed, especially for longer-cavity lasers. (See for example, Huber, R. et al. (2005). "Amplified, frequency swept lasers for frequency domain reflectometry and OCT imaging: design and scaling principles." *Optics Express* 13(9): 3513-3528).

Some examples of sweepable filters that can be used in tunable sources are: 1) piezoelectrically-driven Fabry-Perot filters, 2) unbalanced fiber-based Mach-Zehnder interferometers, 3) distributed Bragg reflectors (DBR), 4) distributed feed-back (DFB) in the gain medium of the laser itself, and 5) rotating gratings outside the laser cavity. For most filter types, especially the first four, smaller sweep ranges are more easily achieved than large sweep ranges. For example, a semiconductor-based DBR, tuned by carrier density, can change the refractive index by 1%, resulting in a tuning range of 1%. The desired tuning range for pure SS-OCT of biological samples is at least 25 nm, which is 2% of a typical laser wavelength of 1310 nm. Each of these filter types can be naturally adapted to pass several wavelengths simultaneously, because they are based on interference and can operate on multiple orders of interference simultaneously.

In this invention, a continuously swept multi-wavelength laser is combined with an optical multi-channel receiver. The multi-wavelength laser emits several optical frequencies or wavelengths simultaneously. This source covers a broad frequency range in a short time by sweeping the set of individual lasing frequencies so that each lasing frequency covers a portion of the full spectrum. The individual lasing optical frequencies are swept over a relatively small range between neighboring lasing frequencies. As a result, the cost of the FD-OCT system can be markedly reduced. The proposed continuously swept multi-wavelength laser can also be made at a low cost as it is only slightly different from standard tunable semiconductor lasers for telecom applications. An additional very beneficial feature of the invention is that the time required for each A-scan can now be substantially reduced, which means that the A-scan rate can be substantially increased relative to the single lasing wavelength swept-source. The individual lasing frequencies simultaneously excite the OCT interferometer, and a multi-channel optical receiver can separate and record the resulting interference signals from the individual optical frequencies. The required multi-channel receiver is now commercially available at a relatively low cost and the price is still continuously dropping as a result of the development for optical fiber telecom applications.

SUMMARY OF THE INVENTION

The present invention is an alternative Fourier domain optical coherence tomography (FD-OCT) system comprising a swept multi-wavelength laser, an optical interferometer and a multi-channel receiver (detector). The optical interferometer includes a beam splitter, which may be, for example, a fiber optic coupler, for separating the light along a sample and reference path. Light returning from both paths is combined and the combined light is measured by the detector.

The present invention also includes a method for performing Fourier domain optical coherence tomography, comprising the steps of simultaneously sweeping the wavelengths of a multi-wavelength laser, directing the light beam from the swept multi-wavelength laser to an interferometer, and detecting the interfered optical signal using a multi-channel receiver. By selecting a comb spacing of the multi-wavelength laser to be equal to or greater than the channel width of the multi-channel receiver and by sweeping each lasing wavelength across a spectral width equal to or greater than the laser comb spacing, each individual channel detector will record a partial spectral interferogram. The full spectral interferogram over a broad spectral bandwidth can be obtained by combining the data from the partial spectral interferograms.

A main object of the invention is to reduce the cost of an FD-OCT system and this is achieved by combining a swept multi-wavelength laser with a multi-channel receiver in an optical interferometer. Owing to the fact that the sweep range for each lasing wavelength of a multi-wavelength laser is substantially reduced as compared to that of a swept single wavelength laser that needs to cover the same overall spectral range, such a multi-wavelength laser can hence be fabricated at a relatively low cost as compared to the swept single wavelength laser. Meanwhile, one can also take advantage of the multi-channel receivers that have already been developed for fiber optical communications and are now commercially available at relatively low cost.

Another key advantage is the increase in the speed of each axial scan relative to pure SS-OCT. Since the tuning range for each wavelength of the multi-wavelength laser is substantially reduced, for a given a sweep rate limited by either the filter element or by laser dynamics, the time required to record one interferogram, corresponding to one axial scan, is also substantially reduced.

In some cases, the speed of the sweep over optical frequencies might be limited by the speed of the optical detectors or the digitizers recording the detected signals. In these cases, this invention has the advantage of using these detectors in parallel, with each detector required to record only a section of the full spectral interferogram within the time allowed to complete an axial scan.

A further advantage of this invention is that it can make more efficient use of the laser gain medium. Gain media designed to have broad gain bandwidth, such as quantum dot or dot-in-well based semiconductor optical gain media, are largely inhomogeneously broadened, meaning that distinct portions of the medium contribute to gain at different optical frequencies. All these distinct portions are often pumped simultaneously, such as in typical broadband semiconductor optical amplifiers (SOA) where a largely inhomogeneously broadened gain medium is excited using a single drive current (see for example, Yao J. et al. "Multiwavelength Erbium-Doped Fiber Ring Laser Incorporating an SOA-Based Phase Modulator" *Photonics Technology Letters, IEEE* 17(4): 756-758). In a frequency-swept laser then, some portions of the gain medium must maintain their population inversion for the majority of the sweep period during which these portions do not produce output light. The population inversion relaxes, typically less than one microsecond in a SOA, and must be continuously replenished, by current injection in an SOA. Allowing multiple optical frequencies to lase simultaneously increases the duty cycle during which each portion of the gain medium is producing output light, reducing the power requirements and heat dissipation of the source. Increasing the duty cycle also increases the ratio of lasing output to amplified stimulated emission, which is advantageous because amplified spontaneous emission in the laser output adds noise to the OCT image.

One object of the invention is to make use of existing lasers or adapt their fabrication technologies to the manufacturing of the tunable multi-wavelength laser. In this respect, the multi-wavelength laser can be made based on a sampled grating based semiconductor laser. Such a laser may have two sections, of which one is the lasing section incorporated with a sampled grating that can enable the sweeping of the multiple lasing wavelengths, and the other is an optical amplifier section that can compensate for the change in the output optical power. Alternatively, the tunable multi-wavelength laser can also be made from a tunable Fabry-Perot semiconductor cavity. Such a laser can also have two sections, of which one is a gain section for lasing and the other is a transparent section for sweeping the lasing wavelengths. A separate optical amplifier can also be made next to the laser to boost and also control the optical output power. Furthermore, the tunable multi-wavelength laser can also be made from a tunable ring or race-track semiconductor cavity. Such a laser can again have two sections, of which one is a gain section for lasing and the other is a transparent section for sweeping the lasing wavelengths. A separate optical amplifier can also be made next to the laser to boost and control the optical output powder.

Other types of laser source for the present invention include an extended multi-wavelength cavity laser that is made tunable with at least an optical amplifier and a tunable multi-wavelength filter functioning as part of the laser cavity. The extended long laser cavity is preferably made with optical fiber. Both the optical amplifier and tunable multi-wavelength filter are preferably either integrated optical waveguide based, or optical fiber based or optical fiber pigtailed.

Multi-channel receivers that can be used for the present invention include a monolithically integrated semiconductor multi-channel receiver, and a discrete optical demultiplexer or a series of thin film-DWDM Bandpass filters that can be combined with a series of photodetectors to function as the multi-channel receiver.

These and other features and advantages of the present invention will become more readily apparent to those skilled in the art upon review of the following detailed description of the preferred embodiments taken in conjunction with the accompanying drawings.

DETAILED DESCRIPTION OF THE INVENTION

Figure 1:
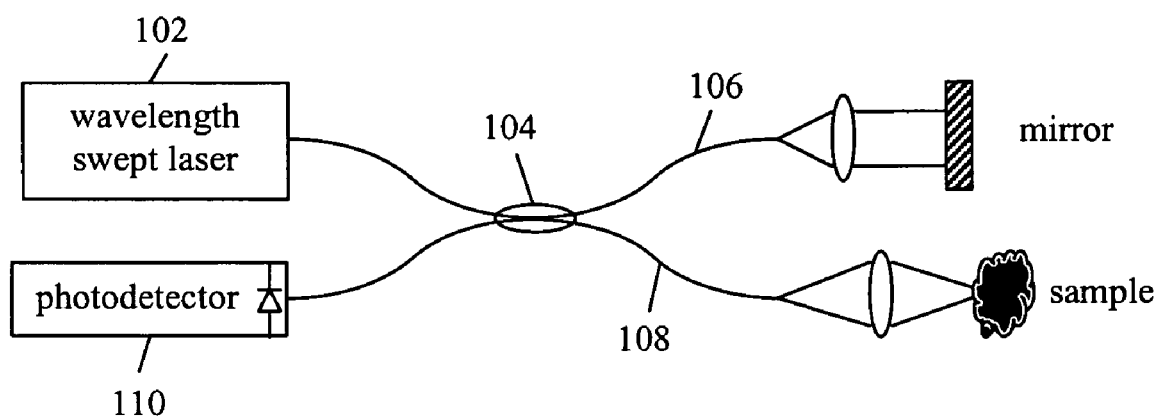
FIG. 1 shows the basic configuration of a pure SS-OCT system.
Figure 2:
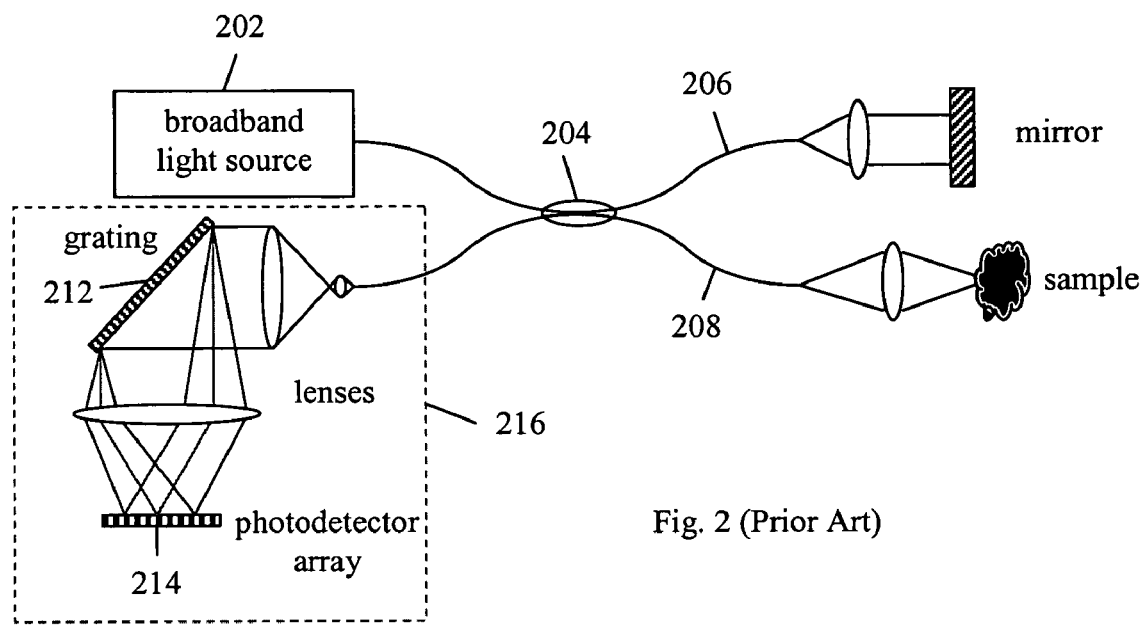
FIG. 2 shows the basic configuration of a pure SD-OCT system.
Figure 3:
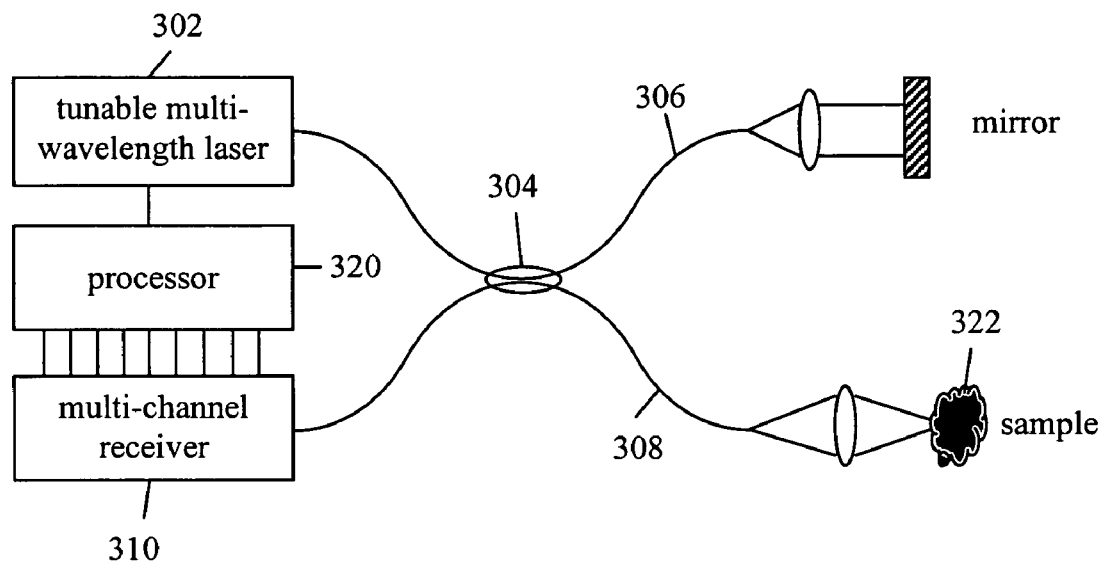
FIG. 3 shows the basic configuration of the presently invented FD-OCT system.
Figure 3:
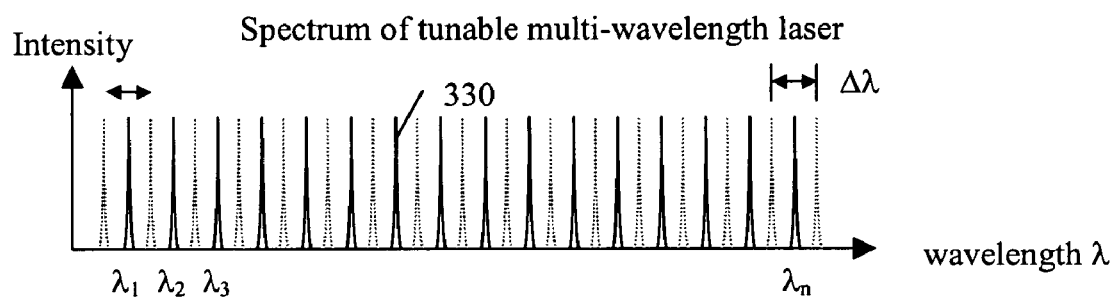

FIG. 3 shows a basic configuration of the present invention. Light from a tunable multi-wavelength laser 302 is split via a beam splitter, for example, fiber coupler 304, into a reference arm 306 and a sample arm 308 of an interferometer. Light returning from the reference arm and the sample is combined, either with the same splitter as shown in FIG. 3 or another beam combining element as is known in the interferometry art. The combined, interfered light is sent to a detector, in this case, multi-channel receiver 310. A processor 320 obtains the spectral interferogram data from the multi-channel receiver 310, synchronized with the sweeping of the multi-wavelength laser 302. For example, the circuitry which drives the frequency sweep of the laser can supply a synchronization signal to the processor.

The processor combines the samples from the individual channels to form a full spectral interferogram and carries out a Fourier transform of the spectral interferogram to provide the information of the reflectance distribution along the depth within the sample 322, in a similar way as described by Huber, R. et al. (2005). "Amplified, frequency swept lasers for frequency domain reflectometry and OCT imaging: design and scaling principles" *Optics Express* 13(9): 3513-3528. Note that the reflectance detected includes not only specular reflections, but also other scattering processes that return light to the multi-channel receiver. In a preferred embodiment, the tunable multi-wavelength laser 302 simultaneously produces a comb spectrum 330 of n lasing wavelengths ($\lambda_1$ to $\lambda_n$) that are all simultaneously swept across a range of optical frequency that is comparable to or greater than the channel spacing $\Delta\lambda$ of the comb spectrum 330, and the channel spacing (also called the free spectral range) $\Delta\lambda$ of the comb spectrum 330 is comparable to or greater than the individual channel width of the multi-channel receiver 310.

The tuning range now required for each lasing wavelength of the multi-wavelength laser 302 is reduced by approximately n times as compared to that of a tunable single wavelength laser that covers the same overall broadband spectral range. Each photodetector in the multi-channel receiver 310 will sequentially receive a partial spectral interferogram covering approximately a bandwidth of the corresponding channel. If the channels of the multi-channel receiver are spectrally spaced next to each other or more preferably, slightly overlapping, the overall spectral interferogram can be completely covered by the channels. In other words, the overall spectral interferogram as a function of wavelength covering the whole broadband spectrum is now divided into many parallel wavelength band channels and a combination of all the channel detector signals will produce substantially the same spectral interferogram as would have been obtained by a pure SS-OCT or SD-OCT system covering the same overall wavelength range.

Figure 4:
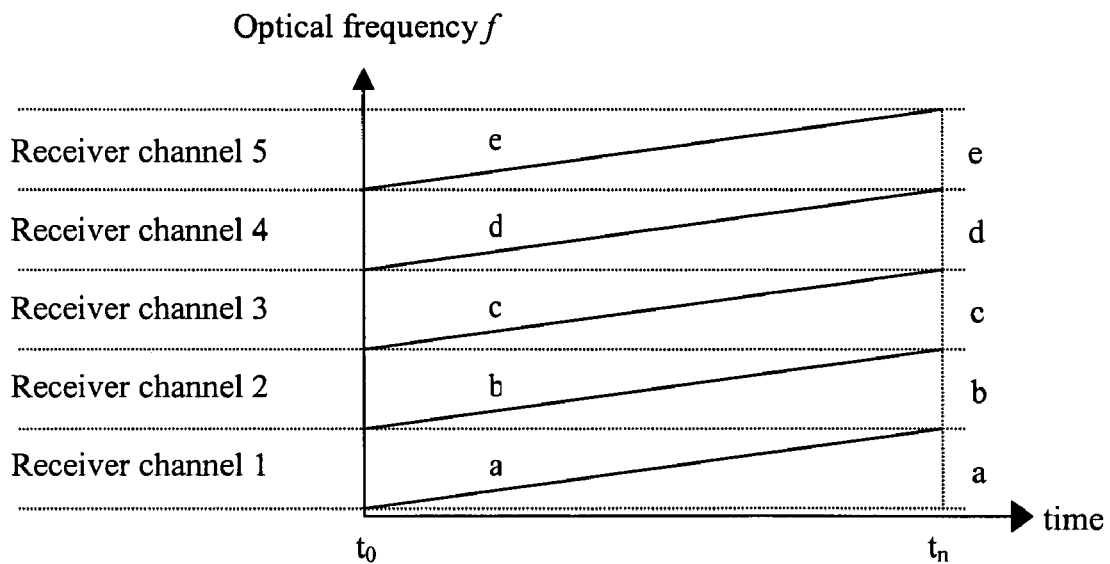
FIG. 4(a) shows a simple case in which the free spectral range of the multi-wavelength laser is matched to the individual channel width of the multi-channel receiver, and the simultaneous outputs of the multi-wavelength laser, labeled 'a', 'b', 'c', etc., is swept across the individual channel width of the multi-channel receiver, labeled '1', '2', '3', etc.
FIG. 4(b) shows a more general case in which the free spectral range of the multi-wavelength laser is greater than the individual channel width of the multi-channel receiver, and the simultaneous outputs of the multi-wavelength laser is swept across a range greater than the free spectral range of the multi-wavelength laser.
FIG. 4(c) shows the acceptance bands of each receiver channel with roll-off at the two sides of the pass band, and the overlap between neighboring channels.
Figure 4:
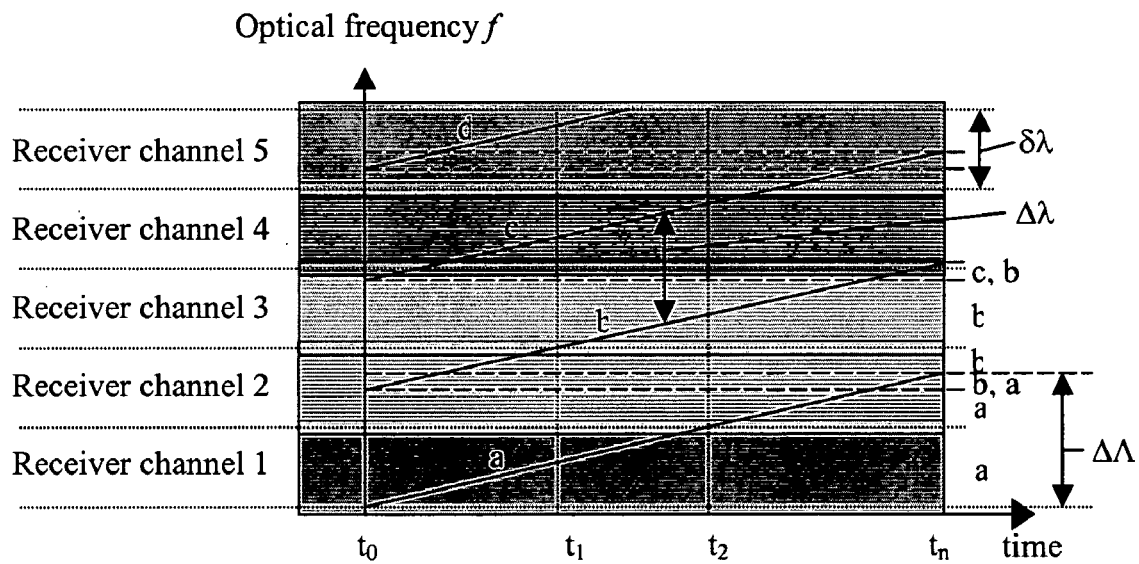
Figure 4:
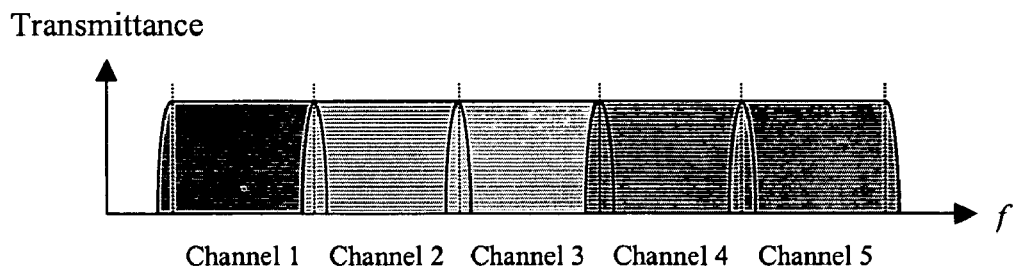

FIG. 4(a) shows a simple configuration of the lasing optical frequencies, labeled 'a', 'b', 'c', etc., being swept across the partial spectral ranges, labeled receiver channel '1', '2', '3', etc., recorded by the individual channels of the multi-channel receiver 310. In this case, the free spectral range $\Delta\lambda$ of the multi-wavelength laser 302 is matched to the individual channel width, labeled receiver channel '1', '2', '3', etc., of the multi-channel receiver 310. It can be clearly seen that under perfect conditions, each channel of the multi-channel receiver 310 will receive a partial spectral interferogram covered by each corresponding swept lasing wavelength of the multi-wavelength laser 302 and a combination of all the partial spectral interferograms will enable one to obtain the full overall spectral interferogram. However, a perfect match among the free spectral range of the multi-wavelength laser, the sweeping range of each lasing wavelength, and the individual channel spectral window of the multi-channel receiver, is difficult to achieve. In addition, the individual channel passband of the multi-channel receiver generally has some degree of roll-off at the two edges. Consequently, the simple configuration of FIG. 4(a) may not be implementable in practice.

FIG. 4(b) shows a more general case in which the free spectral range $\Delta\lambda$ of the multi-wavelength laser is greater than the individual channel width $\delta\lambda$ of the multi-channel receiver, and each of the simultaneous outputs, labeled 'a', 'b', 'c', etc., of the multi-wavelength laser is swept across a range $\Delta\Lambda$ greater than the free spectral range $\Delta\lambda$ of the multi-wavelength laser. This general configuration will ensure that the full overall spectral range is completely covered by the multi-wavelength laser as well as the multi-channel receiver so that the combined spectrum is covered without gaps. As the multi-wavelength source is swept, the individual lasing optical frequencies, labeled 'a', 'b', 'c', etc., move across the partial spectral ranges $\delta\lambda$ covered by channels labeled '1', '2', '3', etc. The signal in each channel is recorded as illustrated in FIG. 4(b). Receiver channel 1 records the partial spectral interferogram at the optical frequencies indicated by the a's from time $t_0$ to $t_2$. Receiver channel 2 first records the spectral interferogram at the optical frequencies indicated by the b's from time $t_0$ to $t_1$, followed by recording no signal for a time duration from time $t_1$ to $t_2$, and then records the spectral interferogram at the frequencies indicated by the a's from time $t_2$ to $t_n$. As the spacing $\Delta\lambda$ of the individual lasing optical frequencies is greater than the spacing $\delta\lambda$ of the receiver channels, the multi-wavelength laser outputs 'a' and 'b' do not simultaneously illuminate receiver channel 2.

As part of the calibration of the system, one can record, as a function of time in a sweep of the source, the optical frequencies received by each channel of the multi-channel receiver. In operation, the multi-channel receiver is synchronized with the multi-wavelength laser via a processor such as a personal computer (PC) and the progress of the sweep can be monitored, for example as described by Huber et al. (*Optics Express* 13(9): 3513-3528.). The simultaneously lasing optical frequencies will likely maintain a fixed relationship to each other, depending on the type of source. For lasers with interferometer-based filters, the simultaneously lasing optical frequencies satisfy a common interference condition, differing only in the integer order of interference. Therefore, in many cases monitoring only one of the simultaneously-lasing optical frequencies is sufficient to know the location of each frequency in the set.

The recorded partial spectral interferograms from the individual channels are combined to form the combined spectral interferogram. If the acceptance bands of each receiver channel are not strictly square pass band but with roll-off at the two sides of the pass band which is generally the case, and there is overlap between neighboring channels in the multi-channel receiver as shown in FIG. 4(c), then we have multiple measurements of the spectral interferogram at the same optical frequency by two neighboring channels near the border region. Within the range of wavelengths where the acceptance bands of two detectors overlap, each of the two detectors receives a portion of the interfered light returned from the interferometer. These measurements can be averaged in the combined spectral interferogram. The sweep ranges of the individual lasing frequencies may overlap as is shown in FIG. 4(b), where horizontal dashed lines indicate the overlap of the sweep ranges. In this case we have multiple measurements of the spectral interferogram, these measurements being interspersed in optical frequency, as illustrated on the right side of FIG. 4(b) by the sequence 'b, a' and 'c, b' in the combined spectrum. The combined measurements from all receiver channels may be non-uniformly-spaced in optical frequency. This set of combined measurements is preferably re-sampled at uniformly-spaced optical frequencies, such re-sampling is common practice in FD-OCT. The re-sampled spectral interferogram is then processed by the processor in the same way as for the pure SS-OCT or pure SD-OCT cases, as described by Huber, R. et al. (2005). "Amplified, frequency swept lasers for frequency domain reflectometry and OCT imaging: design and scaling principles" *Optics Express* 13(9): 3513-3528; and Choma, M. A. et al. (2003). "Sensitivity advantage of swept source and Fourier domain optical coherence tomography." *Optics Express* 11(18): 2183-2189.

As is well known to those skilled in the art, the speed of a pure SS-OCT system is practically limited by the sweeping time of the tunable laser to cover the whole broad spectral band rather than by the response speed of the photodetector.

Due to the parallel nature of the multiple channels and the reduced tuning range for each lasing wavelength of the tunable multi-wavelength laser, the overall time required to capture the whole spectral interferogram over the whole broad spectrum range for each A-scan can thus be reduced many fold as compared to the pure SS-OCT case as long as each channel detector can respond fast enough, which is generally the case. In other words, the speed for each A-scan can be increased by a factor approximately equal to the number of lasing wavelengths.

In the preferred embodiment, the light source is a tunable multi-wavelength laser or a broadband source such as a superluminescent diode followed by a tunable comb filter that should generate at least two discrete wavelengths and the detector should have at least two channels for measuring two spectral regions. In order to achieve a reasonable benefit from the subject invention, it is desirable that light source should generate at least ten discrete wavelengths and preferably between 10 and 40 and most preferably between 10 and 20 discrete wavelengths. The detector should have a corresponding number of channels to detect a spectral region corresponding to the scan ranges for each of those discrete wavelengths. The scanning range for each wavelength should be at least 0.5 nm and more preferably at least 1.0 nm and preferably in the range of 1.0 nm to 5.0 nm.

The particular wavelengths selected will depend upon the application. For example, in the case of ocular measurements, it is know that diagnostic OCT is typically performed in the near infrared region of the spectrum, from 700 nm to 1600 nm.

In terms of cost, the presently invented FD-OCT system will have a substantial advantage. As will be elaborated later, the proposed swept multi-wavelength laser can be fabricated using well-established technologies similar to those used for the tunable semiconductor lasers made for fiber optic telecommunication applications. The multi-channel receiver has already been developed for fiber optic communication applications and is hence commercially available at low cost.

It could perhaps also be appreciated by those skilled in the art that the pure SS-OCT configuration and the pure SD-OCT configuration are actually two extreme cases of the presently invented alternative FD-OCT configuration. In fact, when the channel number is reduced to 1, the invented alternative FD-OCT configuration is reduced to the pure SS-OCT case. On the other hand, when the channel number increases to the point (e.g. 2000 channels) that a useful spectral interferogram can be taken from the detectors without sweeping the lasing wavelengths, the invented FD-OCT system is then effectively reduced to the pure SD-OCT case. Practically speaking, there is a fundamental limit to the number of lasing wavelengths that can be generated by a simultaneous multi-wavelength laser. That limit is set by either the lasing spectral line width or mode competition as a result of homogeneous broadening of the gain optical medium of the laser. Hence there is a limit to the minimum spacing that can be achieved between two neighboring simultaneously lasing wavelengths. In theory, when the spectral resolution of the array spectrometer of a pure SD-OCT or the spectral range covered by each pixel of the line scan camera of the spectrometer is equal to the lasing line width of a multi-wavelength laser, the range required to sweep each lasing wavelength across each channel spacing is reduced to zero and the multi-wavelength laser can be viewed as effectively functioning the same as a broadband light source such as a superluminescent diode.

The multi-channel receiver is used in this invention in a way distinct from the line-scan camera in a pure SD-OCT configuration. Each channel in the multi-channel receiver records a time-dependent optical power encoding part of the overall spectral interferogram, while each pixel in a line-scan camera used for pure SD-OCT records one static power level per A-scan. The level of parallelism can be easily adjusted in the multi-channel receiver.

In terms of system-level implementation of the present invention, it should be realized that the illustrated system configuration is only a basic representation and many variations exist. For example, the optical paths can be fiber optic or bulk optic or a combination of each type. Various optical components can be included in the optical path to manipulate the beam of light. For example, one or more optical circulator(s) can be used in various parts of the interferometer to enable high optical power efficiency and also dual balanced detection as is well known to those skilled in the art (U.S. Pat. No. 6,657,727, U.S. Provisional patent application No. 60/629,492). Various optical polarization manipulation components, including polarization beam splitters, wave plates, Faraday rotators, and polarizers can all be employed for various purposes such as polarization sensitive OCT (U.S. Pat. No. 5,459,570) or polarization diversity detection (U.S. Pat. No. 5,202,745). Multiple optical phase control elements can also be used to enable multi-phase detection (US20040239938, WO04111929). In addition, an optical frequency shifter or optical phase modulator can also be used in either the sample path or the reference path to remove the mirror image and to double the depth scan range (see for example, Yun, S. H. et al. (2004) "Removing the depth-degeneracy in optical frequency domain imaging with frequency shifting." *Optics Express* 12(20): 4822-4828; and Zhang, J. et al. (2005). "Removal of a mirror image and enhancement of the signal-to-noise ratio in Fourier-domain optical coherence tomography using an electro-optic phase modulator." *Optics Letters* 30(2): 147-149).

The key optical components for the present invention are the swept multi-wavelength laser and the multi-channel receiver. Fortunately, in the past several years, there has been a lot of development on DWDM (dense wavelength division multiplexing) optical components for optical fiber telecommunication applications. Hence the presently invented alternative FD-OCT system can substantially take advantage of these low cost optical devices. Of particular interest are the fact that broadband semiconductor optical amplifiers and broadband discretely tunable semiconductor laser have already been developed, and the fact that multi-channel demultiplexers as well as multi-channel receivers have also already been well developed.

In particular, the technology to incorporate sampled or superstructure distributed feedback gratings directly on a semiconductor laser chip with a comb multi-wavelength reflection spectrum has been well developed (see for example, U.S. Pat. No. 4,896,325, U.S. Pat. No. 5,325,392, US20030128724, and US20040228384). While for optical fiber telecom applications, two multi-wavelength filters of different comb width are generally used as front and back mirrors to take advantage of the Vernier effect to produce discretely tunable single lasing wavelength over a large lasing bandwidth (see for example U.S. Pat. No. 4,896,325), the concept of a tunable multi-wavelength comb filter grating can be directly applied to produce swept multi-wavelength semiconductor lasers.

Figure 5:
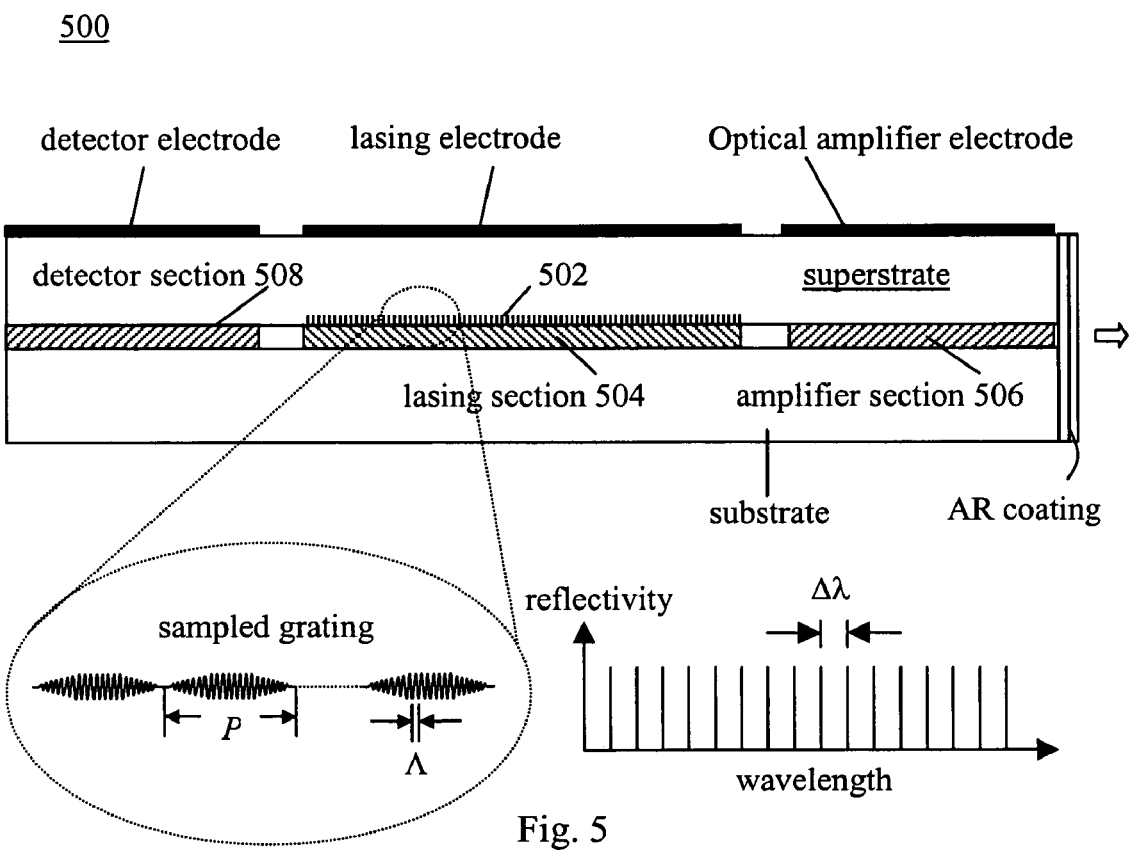
FIG. 5 shows an example of a tunable multi-wavelength monolithic semiconductor laser that has incorporated a sampled grating near the gain section.

According to one aspect of the present invention, a tunable multi-wavelength filter 502, such as a sinc-sampled grating (see for example U.S. Pat. No. 5,325,392 and Ibsen, M. et al. (1998) "Sinc-sampled fiber Bragg gratings for identical multiple wavelength operation." *Photonics Technology Letters, IEEE* 10(6): 842-844) can be made directly on or near the lasing section 504 of a multi-wavelength semiconductor laser 500 as shown in FIG. 5. By tuning the effective refractive index of the sampled grating 502 electronically through, for example, current injection or the Franz-Keldysh effect, a high speed swept multi-wavelength laser can be realized. Such a laser will inherently enable mode-hop-free multi-wavelength sweeping as the simultaneously lasing multiple wavelengths are those supported by the resonant structure of the laser waveguide 500 itself. As an example, the semiconductor laser can have two sections with one being the lasing section 504 that has incorporated the sinc-sampled grating and the other section being an optical amplifier section 506. Furthermore, a photodetector section 508 can also be incorporated on the opposing side of the optical amplifier section 506 to monitor the optical output power. When the lasing section 504 has its injection current modulated to sweep the multiple lasing wavelengths, the optical amplifier section 506 can be modulated in synchronization to provide a gain or loss that compensates the optical power change, so as to maintain a constant output optical power. A very advantageous benefit of the sampled grating based tunable multi-wavelength semiconductor laser 500 is that the length of the sampled-grating laser can be made as long as practically reasonable, which will enhance the optical output power. The price to pay is perhaps a larger area of the laser chip and hence a higher cost per die. But since the die cost is typically much less than the device packaging cost, the increase in the die cost will hence not affect the device cost much.

As is well known to those skilled in the art, the maximum achievable Bragg wavelength tuning by electrical current injection into a distributed Bragg grating waveguide fabricated on a typical III-V semiconductor waveguide is about 5 to 10 nm for a near infrared center wavelength (see for example, U.S. Pat. No. 5,325,392). This tunable range is not enough for a single wavelength sweep across a broad spectral range of 25 to 200 nm but is enough to cover the channel spacing of DWDM based standard multi-channel receivers. In fact, the multi-channel receivers designed for standard DWDM ITU (International telecommunication union) grid has a channel spacing of $\Delta f=50, 100, 200, 400, 800$ GHz, which, for a center wavelength of $\lambda_c=1.3$ μm, corresponds to a wavelength spacing of 0.282, 0.564, 1.127, 2.254 and 4.508 nm respectively. It can thus been seen that each of the above-mentioned channel spacing is all within the tunable range that can be achieved by current-injection into a sampled grating based multi-wavelength semiconductor laser.

The corresponding sampling period P as shown in FIG. 5 can be determined (see for example, Ibsen, M. et al. (1998). "Sinc-sampled fiber Bragg gratings for identical multiple wavelength operation." *Photonics Technology Letters, IEEE* 10(6): 842-844.) to be respectively equal to $P_{50\,GHz} \approx 920$ μm, $P_{100\,GHz} \approx 460$ μm, $P_{200\,GHz} \approx 230$ μm, $P_{400\,GHz} \approx 115$ μm and $P_{800\,GHz}$ μm, which are also within the fabrication dimension range for a practical device (see for example, Jayaraman, V. et al. (1993). "Theory, design, and performance of extended tuning range semiconductor lasers with sampled gratings." *Quantum Electronics, IEEE Journal of* 29(6): 1824-1834).

Figure 6:
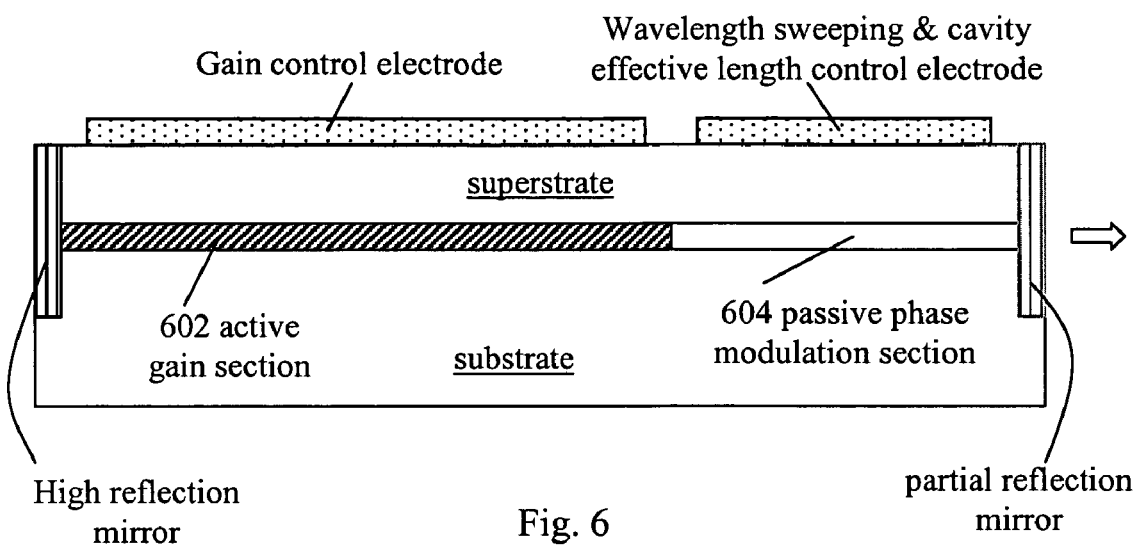
FIG. 6 shows a tunable multi-wavelength monolithic Fabry-Perot (F-P) semiconductor laser that comprises at least an active gain section and a passive phase modulation section.

According to another aspect of the present invention, the swept multi-wavelength laser can also be made based on a tunable Fabry-Perot (F-P) laser cavity, simply because an F-P cavity is also a comb multi-wavelength filter. FIG. 6 shows an exemplary design of an F-P cavity based tunable multi-wavelength laser 600. In a preferred embodiment as shown in FIG. 6, the F-P cavity is composed of two sections, a gain section 602 and a transparent phase modulation section 604 for sweeping the multiple lasing wavelengths. By dividing the F-P cavity into two sections, the output power of the multi-wavelength laser can be maintained substantially constant by a closed loop feedback control of the electrical current injected into the gain section 602 and a fast sweep of the lasing comb spectrum can be achieved by rapidly modulating the refractive index of the transparent section 604 through electrical current or voltage applied to the electrode of this section. Furthermore, a separate optical amplifier section (not shown) can also be fabricated or arranged next to the F-P cavity laser 600 for amplifying and controlling the output optical power.

As is well known to those skilled in the art, the free spectral range or comb width of a F-P cavity is given by $\Delta f=c/(2\, n_{eff}\, L_{eff})$, where c is the speed of light in vacuum, $n_{eff}$ is the effective refractive index of the F-P cavity, and $L_{eff}$ is the effective length of the F-P cavity. For InP with $n_{eff} \approx 3.25$, and $\Delta f=50, 100, 200, 400, 800$ GHz, the corresponding effective F-P cavity length is found to be $L_{eff} \approx 920$ μm, 460 μm, 230 μm, 115 μm and 57.5 μm respectively. While last two cavity lengths might be too small for the desired optical output power, the tuning range required, and die handling or device packaging, the first three lengths are all reasonable for practical device fabrications.

Although semiconductor lasers with a small number of F-P cavity longitudinal modes are now commercially available (Vilokkinen, V. et al. (2004). "Reliability analysis of AlGaInAs lasers at 1.3 μm." *Electronics Letters* 40(23): 1489-1490), they are single-section devices with narrow gain bandwidth. In order to use the F-P cavity approach to greater advantage of the present invention, a few adjustments to the laser can be made. The first is to substantially increase the bandwidth of the gain curve to cover the desired overall spectral bandwidth; this has already been demonstrated in recent years through, for example, quantum well intermixing (see for example, U.S. Pat. No. 6,617,188). The second improvement is to make the F-P cavity into at least two sections including a gain section and a second transparent section for refractive index modulation and hence lasing wavelength sweeping. This issue can also be addressed by quantum well intermixing (see for example, U.S. Pat. No. 6,878,562).

The third issue is the precision control of the length of the F-P cavity. This precision control may be required because the accuracy of the spacing between two neighboring lasing wavelengths depends on the accuracy with which the two facets of the cavity are formed. Fortunately, this is not a big problem for the present invention, as the multiple lasing wavelength spacing does not need to exactly match the channel width of the multi-channel receiver and can be larger than the receiver grid. Reconstruction of a full spectral interferogram from the partial spectral interferograms will succeed as long as the lasing comb spacing is equal to or greater than the channel width of the multi-channel receiver and is less than the overall sweep range.

If precision comb spacing is still preferred, lithography can be used to define the cavity length and to directly dry etch optically smooth facets to define the two end mirrors for the F-P cavity (see for example, Behfar A. et al. (2005) "Etching Advances—Replacing cleaved facets with etched facets produces improved lasers" SPIE oemagazine, February 2005, p 27).

It should be noted that the same discussion made on the F-P cavity based swept multi-wavelength laser can be easily extended to a semiconductor ring or race-track cavity. Therefore, a ring cavity based tunable multi-wavelength laser is also a possible light source for the present invention. The ring or race-track cavity based semiconductor laser preferably also has at least two sections, of which one is a gain section for lasing and the other is a transparent index modulation section for sweeping the lasing wavelengths. In addition, a separate optical amplifier can also be made next to the laser to boost the optical output power.

An issue that might need to be considered for a sampled grating or F-P cavity or ring cavity based multi-wavelength laser is the chromatic dispersion in the refractive index of the waveguide material. This dispersion will cause the lasing optical frequencies to be non-uniformly spaced if the overall optical frequency or wavelength range to be covered is large. In the present invention, the spacing of lasing frequencies does not need to match the spacing of the receiver channels, because reconstruction of the full spectral interferogram as illustrated in FIG. 4(b) does not depend on such a match. Non-uniformity in the spacing of multiple lasing optical frequencies has potential advantage in this application to FD-OCT. Power fluctuations or other disturbances to the source that affect all lasing optical frequencies simultaneously can result in distortions in the combined spectral interferogram. If these distortions are non-uniformly spaced in optical frequency (more precisely, non-uniformly spaced in wavevector in the sample material) then these distortions do not combine to produce a sharp artifact in the reconstructed axial scan, produced by Fourier transform of the spectral interferogram. Intentionally inserting into the cavity a section with large chromatic dispersion can thus be used to suppress such artifacts.

Figure 7:
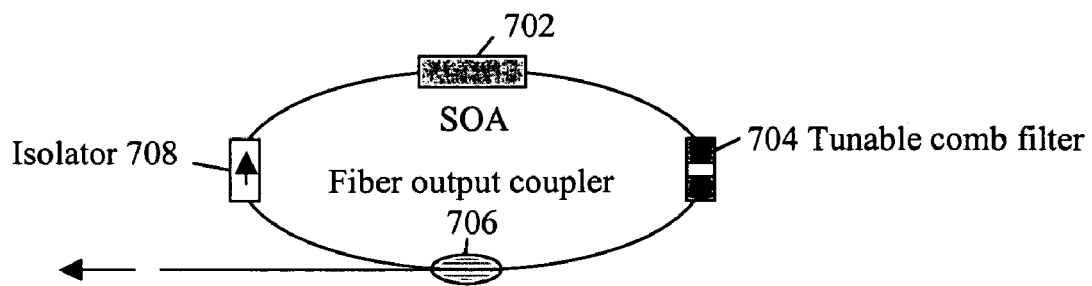
FIG. 7(a) shows swept multi-wavelength fiber ring cavity laser comprising a semiconductor optical amplifier (SOA), a tunable F-P filter, a fiber output coupler and an isolator for unidirectional lasing
FIG. 7(b) shows a swept multi-wavelength fiber F-P cavity laser comprising a highly reflective fiber end mirror on the one side, a partially reflective fiber mirror on the other side, a semiconductor optical amplifier (SOA) and a tunable F-P filter.
FIG. 7(c) shows a swept multi-wavelength fiber quasi-ring cavity laser comprising a tunable sampled Bragg grating (SBG), a fiber coupler, a semiconductor optical amplification, and an isolator.
FIG. 7(d) shows a swept multi-wavelength fiber quasi-ring cavity laser comprising a tunable sampled Bragg grating (SBG), an isolator, and a semiconductor optical amplification.
FIG. 7(e) shows a swept multi-wavelength fiber F-P cavity laser comprising tunable sampled Bragg grating (SBG), a semiconductor optical amplifier and a fiber loop mirror.
Figure 7:
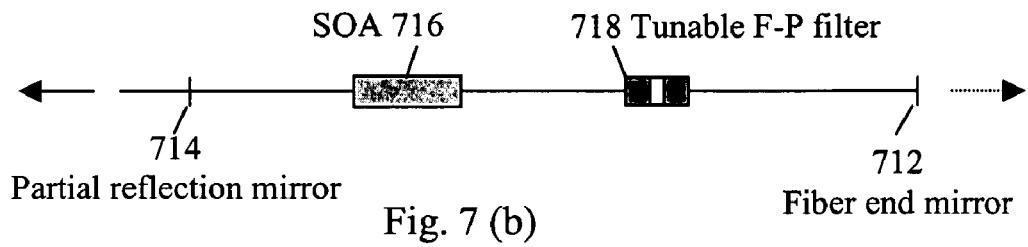
Figure 7:
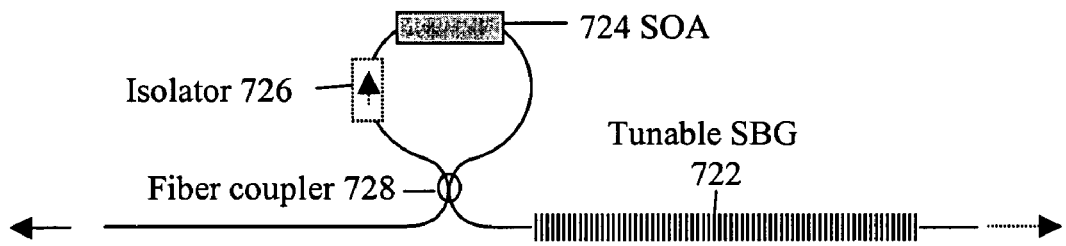
Figure 7:
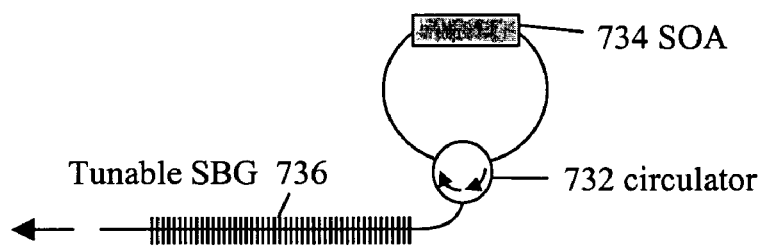
Figure 7:
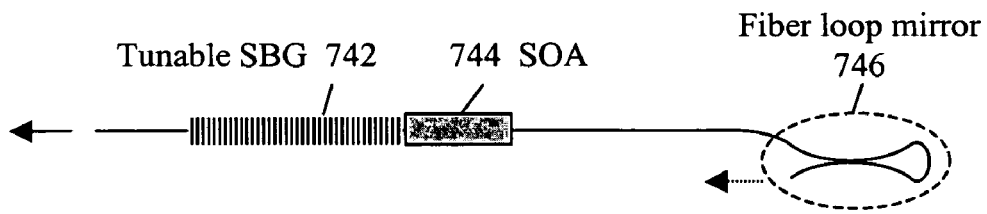

According to another aspect of the invention, a tunable multi-wavelength comb filter can also be incorporated in an extended cavity of a laser. FIGS. 7(a), (b) (c) (d) and (e) show some exemplary configurations of such a design. In these exemplary embodiments, optical fibers and other fiber optic components are preferably used to form an optical resonator with a long enough overall cavity length such that the longitudinal modes of the long cavity are so densely spaced that mode hopping between these longitudinal mode is not a concern any more for OCT applications and the actual multiple lasing wavelengths are determined by a tunable comb filter acting as part of the laser cavity.

In the first exemplary embodiment of FIG. 7(a), a fiber ring cavity includes a semiconductor optical amplifier (SOA) 702, a tunable comb filter 704, a fiber output coupler 706 and, preferably, an isolator 708 for unidirectional lasing as well. With swept multiple wavelength lasing, the amount of tuning required for each lasing wavelength (which translates to the amount of voltage for a PZT stretcher) is substantially reduced as compared to a pure SS-OCT system that covers the same overall spectral range. It should be noted that the tunable comb filter 704 for this and the following exemplary embodiments can be of various types, for example, it can be a piezo-electrically actuated fiber F-P comb filter (see for example, Haber, T. et al. (2002). "Tunable erbium-doped fiber ring laser precisely locked to the 50-GHz ITU frequency grid" *Photonics Technology Letters, IEEE* 12(11): 1456-1458), it can also be a Sagnac interferometer based tunable filter (see for example, Fang, X. et al. (1997). "A subnanosecond polarization-independent tunable filter/wavelength router using a Sagnac interferometer." *Photonics Technology Letters, IEEE* 9(11): 1490-1492) or an unbalanced Mach-Zehnder interferometer based tunable comb filter or a cascaded and/or combined version of the above mentioned transmission filters or other comb filters known to those skilled in the art.

In the second example as shown in FIG. 7(b), a relatively long F-P laser cavity is formed by a highly reflective fiber end mirror 712 on the one side and a partially reflective fiber mirror 714 on the other side. The laser cavity also contains an optical amplifier 716 such as a semiconductor optical amplifier (SOA) and a tunable multi-wavelength comb filter 718 as mentioned above. Note that the highly reflective fiber end mirror 712 can act as an output for optical power monitoring. It can also be replaced by a fiber loop mirror as is well known. By selecting the coupler split ratio to differ slightly from 50/50, a small percentage of light can be tapped from the non-connected fiber port of the loop mirror fiber coupler. The partially reflective mirror 714 on the other side can also be replaced by a combination of a highly reflective end mirror and a fiber tap coupler for laser output coupling.

In the third example as shown in FIG. 7(c), the laser cavity is composed of a quasi-ring and is terminated with a tunable multi-wavelength mirror 722. Preferably, the reflective multi-wavelength comb mirror is a sampled Bragg grating (SBG) such as a sampled fiber Bragg grating (SFBG) that can be tuned. It can also be a current injection based sampled Bragg grating waveguide made on a semiconductor as discussed before. The quasi-ring contains an optical amplifier 724 such as an SOA and may also contain an isolator 726 to enable unidirectional lasing in the quasi-ring. With the isolator, the fiber coupler 728 is preferably a 3 dB coupler which will enable 50% of the lasing power being tapped but a high overall coupling efficiency so that a minimum amount of light returned from the SBG is lost as counter-clockwise propagating wave at the isolator. Without the isolator 726, bidirectional lasing may occur in the quasi-ring and mode competition may suppress one of the clockwise or counter-clockwise waves. In both cases, the optical output from the other side of the SBG can be used for output power monitoring as is known.

As an alternative as shown in FIG. 7(d), a three port circulator 732 can be used to replace both the fiber coupler 728 and the isolator 726 of FIG. 7(c). In this case, the overall optical loss will be substantially reduced and the multi-wavelength laser output can be obtained from the other side of the tunable comb filter or SBG 736.

In addition to a ring or quasi-ring cavity, a tunable reflective multi-wavelength mirror 742 can also be used in an F-P cavity to construct a tunable multi-wavelength laser as shown in FIG. 7(e). This configuration is perhaps the least expensive when compared with other possible configurations of FIGS. 7(a) to (e) and hence might be the most preferred among the extended cavity laser options. Note that the fiber loop mirror 746 can be replaced by a highly reflective fiber end mirror and the laser output can be obtained from either the sampled Bragg grating side or the fiber loop mirror side. Again, the tunable sampled Bragg grating (SBG) can be a sample fiber Bragg grating (SFBG) or a current injection based sampled Bragg grating waveguide made on a semiconductor. In particular, the tunable sampled Bragg grating can be integrated with the optical amplifier on the same semiconductor chip and the facet on the optical amplifier side can be anti-reflection coated and optically connected to a single mode optical fiber that is terminated with a fiber loop mirror.

It should be understood that we have only shown the basic optical elements for the various exemplary configurations, other optical or fiber optical components, including intensity or phase modulators, and especially polarization control components, may be included in or outside the laser cavity for optical beam or polarization manipulation. Although we have constantly mentioned the use of a semiconductor optical amplifier, this is only for the purposes of illustration as other optical amplifiers can also be used, including for example, a rare earth doped fiber amplifier. In addition, the fiber optic path can also be replaced by a free space optic path or a combination of fiber and free space optics.

It should also be understood that the basic principle of operation in terms of the tuning of the F-P cavity and the SBG is similar to what we have discussed previously, the only difference is that for piezo-electrically actuated comb filters, the change in the effective cavity length or effective grating period is caused by a physical dimensional change instead of a change in the effective refractive index. However, if an electro-optical material is used, a change in the effective refractive index can also be used.

Note that other types of multi-wavelength comb filters can all be used, including, for example, long period fiber gratings, few mode fiber Bragg gratings, Mach-Zehnder and Sagnac interferometer filters. In fact, an F-P or SFBG filters may have a limited tuning speed because they need to be mechanically stretched or compressed using for example a piezoelectric actuator. In order to achieve high tuning speed, other mechanism such as those based on electro-optical effect in optical crystals or polymers can all be used. For example, a $LiNbO_3$ waveguide electro-optic polarization controller can be incorporated in a fiber Sagnac loop to act as a high-speed tunable multi-wavelength filter. A $LiNbO_3$ or semiconductor based sampled grating can also be used as a high speed tunable multi-wavelength filter.

Figure 8:
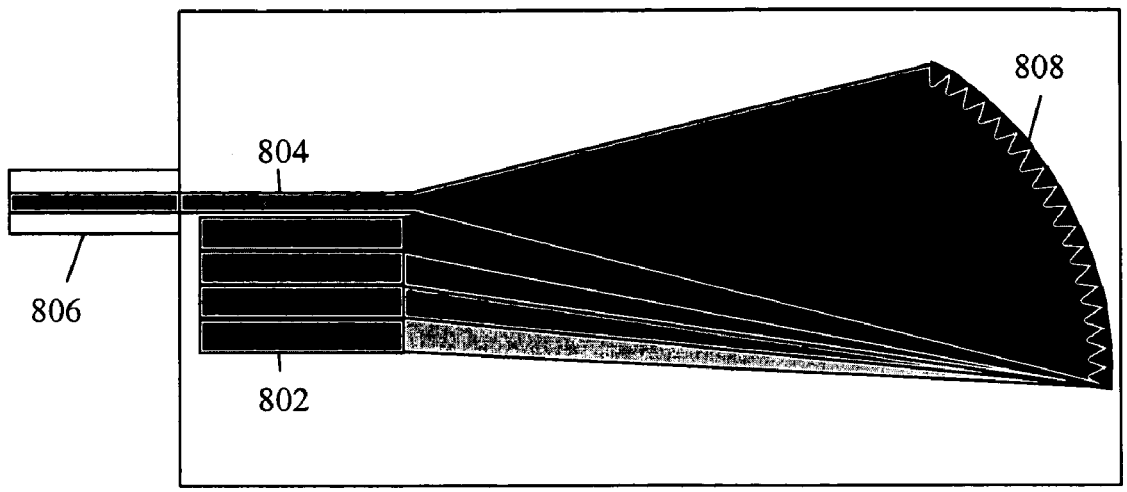
FIG. 8 shows an integrated multi-channel receiver which has monolithically integrated an array of photodetectors with a passive planar waveguide based Echelle grating on a single chip.

A variety of multi-channel receivers are currently available that should be adaptable for use in the subject invention. One example would include a monolithically integrated array of photodetectors 802 with a passive planar waveguide based Echelle grating 808 on a single InP chip as shown in FIG. 8 (see for example, Tolstikhin, V. I. et al. "44-channel optical power monitor based on an echelle grating demultiplexer and a waveguide photodetector array monolithically integrated on an InP substrate", Optical Fiber Communications Conference, Atlanta, Postdeadline Paper PD37, 2003). In this embodiment, light is delivered to the receiver via an input fiber 806 and a passive waveguide 804.

Figure 9:
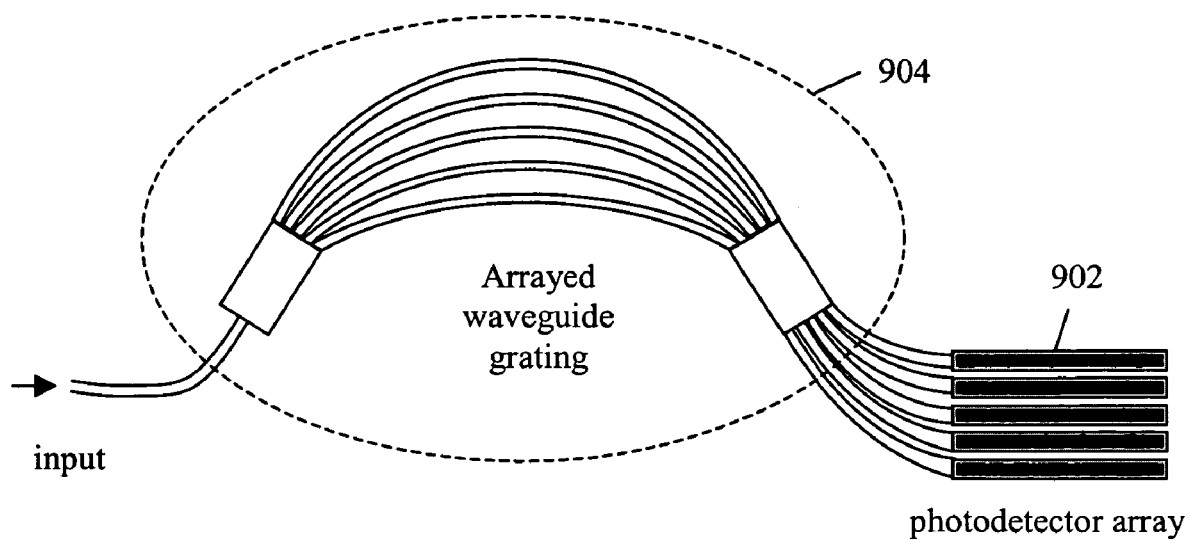
FIG. 9 shows a multi-channel receiver which has monolithically integrated an array of photodetectors with a passive arrayed waveguide grating (AWG) on a single InP chip.

Another example of a receiver is shown in FIG. 9 and includes a monolithically integrated an array of photodetectors 902 with a passive arrayed waveguide grating (AWG) 904 on a single InP chip (see, for example, Nikoufard, M. et al. "An 8×25 Ghz polarization-independent integrated multi-wavelength receiver" Integrated Photonics Research Topical Meeting, proc. IPR 2004, 30 Jun.-4 Jul. 2004, San Francisco, USA, 2004, p. iTHB2).

Figure 10:
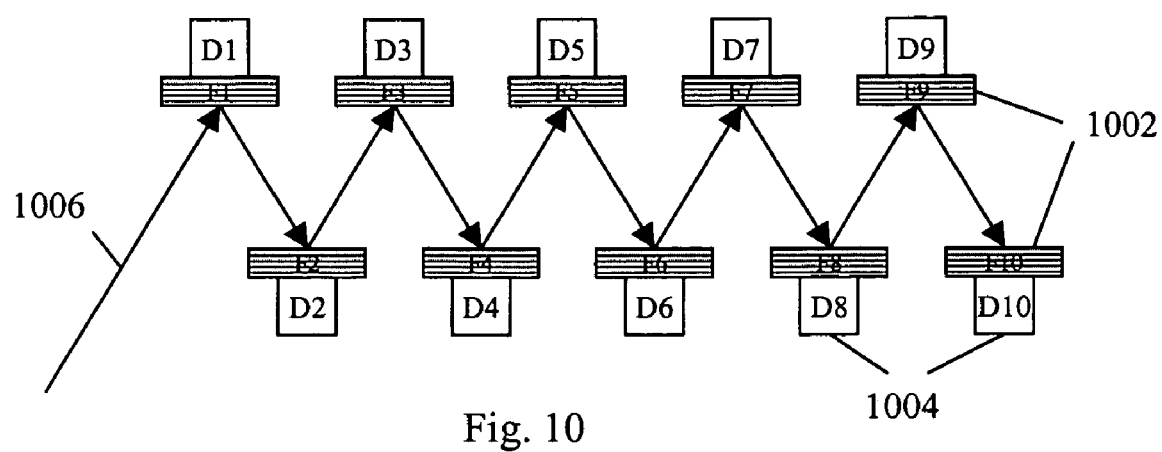
FIG. 10 shows a multi-channel receiver based on an array of thin film optical bandpass filters combined with an array of photodetectors.

Yet another option is shown in FIG. 10, wherein the multi-channel receiver can be based on an array of thin film based optical bandpass filters 1002 combined with an array of photodetectors 1004 as is well known to those skilled in the art of optical fiber communications. In this configuration, a number of thin film based optical interference bandpass filters (for example, F1 to F10 as shown in FIG. 10) are arranged in front of a number of photodetectors (for example, D1 to D10 as shown in FIG. 10) and the interfered OCT beam 1006 is made to bounce in a cascaded or zig-zag way off the series of interference filter covered photodetectors.

As still another option, the multi-channel receiver can also be a combination of an independent optical demultiplexer with a number of photodetectors, as is well known to those skilled in the art of fiber optic communications. The photodetectors can be either directly arranged next to the independent demultiplexer or optically connected to the independent demultiplexer via free space or a number of optical waveguides such as optical fibers. The independent demultiplexer is preferably an arrayed waveguide grating (AWG) made on a planar lightwave circuit, or a holographic Bragg reflector grating (see for example, Greiner, C. M. et al. (2004) "Wavelength Division Multiplexing Based on Apodized Planar Holographic Bragg Reflectors" Applied Optics, Vol. 43, No. 23, pp. 4575-4583) or a planar waveguide Echelle grating (see for example, Janz, S. et al. (2004) "Planar waveguide echelle gratings in silica-on-silicon" Photonics Technology Letters, 16, pp. 503-505), or a bulk blazed diffractive grating.

Since multi-channel receivers are widely used in high speed optical fiber communication systems and are commercially available, there may not be a need for a custom made device for the present invention. On the other hand, as the channels of the multi-channel receiver generally do not have a perfect rectangular pass band spectral response, it might be necessary to make the channel slightly overlapping with each other. In addition, it may be preferred, but not required, to have the lasing frequencies spaced more widely than the receiver channels, including an allowance for the soft edges of the pass bands, in order that each receiver collects spectral interference fringes from at most one wavelength. If two different receivers partially sample the same optical frequency, these samples can be combined to form a better estimate of the interferogram at that frequency during the post-processing steps that combine the partial spectral interferogram from each individual detector.

It should be highlighted that the configuration of the present invention is relatively simple and compact. It is also of lower cost and higher speed. In addition to general optical interferometry for various applications, such as distance measurement, topography and three dimensional measurement of a volume sample, the present invention is particularly beneficial for applications in various optical coherence tomography schemes.

The foregoing description of the invention is presented for purposes of illustration and description and is not intended to be exhaustive or to limit the invention to the precise form disclosed. Many modifications and variations are possible in light of the above teaching. The embodiments were chosen and described to best explain the principles of the invention and its practical application to thereby enable others skilled in the art to best use the invention in various embodiments and with various modifications suited to the particular use contemplated.

We claim:

1. An optical coherence tomography (OCT) system comprising;
   a light source generating light at a plurality of discrete wavelengths simultaneously, said light source being tunable to scan said plurality of discrete wavelengths across a range of wavelengths to generate a plurality of scans of different spectral regions in parallel over time;
   a beam splitter for dividing the light along a sample and a reference path;
   a detector for receiving light returned from both the sample and the reference paths and having a plurality of channels, each channel arranged to measure light within one of said different spectral regions and to simultaneously generate output signals in response to said discrete scanned wavelengths; and
   a processor for analyzing the output signals to derive a reflectance distribution along the sample path.

2. An OCT system as recited in claim 1, wherein the spacing between the discrete wavelengths of the tunable light source is equal to or greater than the width of the spectral regions measured by the detector channels.

3. An OCT system as recited in claim 1, wherein the range of wavelength over which the discrete wavelengths are scanned is equal to or greater than the spacing between the discrete wavelengths.

4. An OCT system as recited in claim 1, wherein the spectral region measured by each detector channel is configured to slightly overlap the spectral region measured by the adjacent channels.

5. An OCT system as recited in claim 1, wherein the processor combines the measurements from the plurality of channels and performs a Fourier analysis to obtain said axial reflectance distribution.

6. An OCT system as recited in claim 1, wherein the light source generates at least ten discrete wavelengths.

7. An OCT system as recited in claim 1, wherein the scanning range of each discrete wavelength is at least 0.5 nanometers.

8. An OCT system as recited in claim 1, wherein the scanning range of each discrete wavelength is at least 1.0 nanometers.

9. An OCT system as recited in claim 1, wherein said detector includes an optical element for spectrally dispersing the light as a function of wavelength and selectively directing different spectral regions to said channels.

10. An OCT system as recited in claim 9, wherein the optical element for spectrally dispersing the light is a grating.

11. An OCT system as recited in claim 1, wherein said detector includes a plurality of bandpass filters for spectrally separating the light as a function of wavelength and selectively directing different spectral regions to said channels.

12. An OCT system as recited in claim 1, wherein said light source is a laser.

13. An OCT system as recited in claim 1, wherein said light source is a superluminescent diode (SLD) followed by a comb filter.

14. An OCT system as recited in claim 1, wherein said light source is a sampled grating based semiconductor laser.

15. An OCT system as recited in claim 1, wherein said light source is a Fabry-Perot based semiconductor laser.

16. An OCT system as recited in claim 1, wherein said light source is a ring or race track cavity based semiconductor laser.

17. An OCT system as recited in claim 1, wherein said light source includes a tunable filter as part of a laser cavity.

18. An OCT system as recited in claim 1, wherein the processor is synchronized with the tuning of the light source.

19. A method of analyzing a sample using optical coherence tomography (OCT) comprising the steps of:
   generating a light output having plurality of discrete wavelengths;
   scanning each discrete wavelength across a range of optical wavelengths to generate a plurality of scans of different spectral regions in parallel over time;
   splitting the light along a sample and a reference path;
   combining the light received back from both sample and reference paths;
   separating the received light into said different spectral regions;
   simultaneously measuring each of the different spectral regions during the scanning step; and
   analyzing the measurements to derive a reflectance distribution along the sample path.

20. A method as recited in claim 19, wherein the spacing between the discrete wavelengths is equal to or greater than the width of the measured spectral regions measured.

21. A method as recited in claim 19, wherein the range of wavelength over which the discrete wavelengths are scanned is equal to or greater than the spacing between the discrete wavelengths.

22. A method as recited in claim 19, wherein the light output is generated by a laser.

23. A method as recited in claim 19, wherein analysis step includes combining the measurements from the different spectral regions and performing a Fourier analysis to obtain said reflectance distribution.

24. A method as recited in claim 19, wherein the light output includes at least 10 discrete wavelengths.

25. A method as recited in claim 19, wherein the scanning range of each discrete wavelength is at least 0.5 nanometers.

26. A method as recited in claim 19, wherein the scanning range of each discrete wavelength is at least 1.0 nanometers.

27. An optical coherence tomography (OCT) system comprising:
   a light source generating light at least ten discrete wavelengths simultaneously, said light source being tunable to scan said plurality of discrete wavelengths across a range of wavelengths to generate a plurality of scans of different spectral regions in parallel over time and wherein the scanning range of each discrete wavelength is at least 1.0 nanometers;
   a beam splitter for dividing the light along a sample and a reference path;
   a detector for receiving light returned from both the sample and the reference paths and having a plurality of channels, each channel arranged to measure light within one of said different spectral regions and to simultaneously generate output signals in response to said discrete scanned wavelengths; and
   a processor synchronized with the tuning of the light source for analyzing the generated output signals to derive a reflectance distribution along the sample path.

28. An OCT system as recited in claim 27, wherein the spacing between the discrete wavelengths of the tunable light source is equal to or greater than the width of the spectral regions measured by the detector channels.

29. An OCT system as recited in claim 27, wherein the range of wavelength over which the discrete wavelengths are scanned is equal to or greater than the spacing between the discrete wavelengths.

30. An OCT system as recited in claim 27, wherein the spectral region measured by each detector channel is configured to slightly overlap the spectral region measured by the adjacent channels.

31. An OCT system as recited in claim 10, wherein said grating is monolithically integrated with a photodetector array, said array defining the channels of the detector.

32. An OCT system as recited in claim 27, wherein detector includes a grating monolithically integrated with a photodetector array, said array defining the channels of the detector.

* * * * *